United States Patent
Kuruma et al.

(10) Patent No.: US 10,166,182 B2
(45) Date of Patent: Jan. 1, 2019

(54) INACTIVATED WHOLE VIRION VACCINE-CONTAINING MICRONEEDLE ARRAY PREPARATION AND METHOD FOR ADMINISTERING THE SAME

(71) Applicants: FUJIFILM Corporation, Tokyo (JP); NATIONAL UNIVERSITY CORPORATION HOKKAIDO UNIVERSITY, Sapporo-shi, Hokkaido (JP)

(72) Inventors: Koji Kuruma, Ashigarakami-gun (JP); Takayoshi Oyamada, Ashigarakami-gun (JP); Toshio Shimada, Ashigarakami-gun (JP); Yoshihiro Sakoda, Sapporo (JP); Hiroshi Kida, Sapporo (JP)

(73) Assignees: FUJIFILM Corporation, Tokyo (JP); NATIONAL UNIVERSITY CORPORATION HOKKAIDO UNIVERSITY, Sapporo-shi, Hokkaido (JP)

( * ) Notice: Subject to any disclaimer, the term of this patent is extended or adjusted under 35 U.S.C. 154(b) by 0 days.

(21) Appl. No.: 15/281,325

(22) Filed: Sep. 30, 2016

(65) Prior Publication Data

US 2017/0014336 A1 Jan. 19, 2017

Related U.S. Application Data

(63) Continuation of application No. PCT/JP2015/060427, filed on Apr. 2, 2015.

(30) Foreign Application Priority Data

Apr. 4, 2014 (JP) ................................ 2014-077603

(51) Int. Cl.
*A61K 39/12* (2006.01)
*A61K 39/145* (2006.01)
*A61K 9/00* (2006.01)
*A61K 39/00* (2006.01)

(52) U.S. Cl.
CPC ............ *A61K 9/0021* (2013.01); *A61K 39/12* (2013.01); *A61K 39/145* (2013.01); *A61K 2039/5252* (2013.01); *A61K 2039/545* (2013.01); *C12N 2760/16134* (2013.01); *C12N 2760/16234* (2013.01)

(58) Field of Classification Search
None
See application file for complete search history.

(56) References Cited

U.S. PATENT DOCUMENTS

| 9,028,463 B2 | 5/2015 | Nozaki et al. |
| 2008/0102192 A1 | 5/2008 | Johnson et al. |
| 2011/0112509 A1 | 5/2011 | Nozaki et al. |
| 2013/0287832 A1 | 10/2013 | O'Hagan et al. |
| 2014/0037694 A1 | 2/2014 | Morimoto et al. |

FOREIGN PATENT DOCUMENTS

| JP | 2007-530680 A | 11/2007 |
| JP | 2008-520370 A | 6/2008 |
| JP | 2012-41329 A | 3/2012 |
| JP | 2012-90767 A | 5/2012 |
| WO | 2005/099751 A2 | 10/2005 |
| WO | 2005/099751 A3 | 10/2005 |
| WO | 2010/001671 A1 | 1/2010 |
| WO | 2012/115222 A1 | 8/2012 |

OTHER PUBLICATIONS

International Preliminary Report on Patentability issued from the International Bureau in counterpart International Application No. PCT/JP2015/060427, dated Oct. 13, 2016.
Extended European Search Report dated Feb. 16, 2017, from the European Patent Office in counterpart European Application No. 15774458.2.
Sullivan, S., et al., "Dissolving polymer microneedle patches for influenza vaccination", Nature Medicine, vol. 16, No. 8, published online Jul. 18, 2010, pp. 1-14, XP002666152.
The Academy of Pharmaceutical Science and Technology, Japan, Proceedings of the 28th Annual Conference, verbal announcement No. 23-3-14 "Analysis of immunity-inducing characteristics of transdermal influenza vaccine preparation in clinical research", 1 page (2013).
Naoki Okada, "From Basic Principles to Clinical Applications on Transcutaneous Vaccine", Journal of the Pharmaceutical Society of Japan, 2013, pp. 1363-1372, vol. 133(12).
Shohei Koyama, et al., "Plasmacytoid Dendritic Cells Delineate Immunogenicity of Influenza Vaccine Subtypes", Science Translational Medicine, Mar. 31, 2010, 10 pages, vol. 2, Issue 25.
International Search Report for PCT/JP2015/060427 dated May 26, 2015 [PCT/ISA/210].
Written Opinion for PCT/JP2015/060427 dated May 26, 2015 [PCT/ISA/237].
Office Action dated Jul. 18, 2017 from the Japanese Patent Office in counterpart Japanese Application No. 2016-511994.
Office Action dated Sep. 26, 2017 from the Japanese Patent Office in counterpart Japanese Application No. 2016-511994.

*Primary Examiner* — Benjamin P Blumel
(74) *Attorney, Agent, or Firm* — Sughrue Mion, PLLC (57) ABSTRACT

Provided is a microneedle. The microneedle array includes a needle portion, which contains an inactivated whole virion influenza vaccine, and a sheet portion. Also provided is an administration method in which the microneedle array is administered and then administered secondly after an interval of equal to or greater than 24 hours and less than 2 months.

7 Claims, 5 Drawing Sheets

INACTIVATED WHOLE VIRION VACCINE-CONTAINING MICRONEEDLE ARRAY PREPARATION AND METHOD FOR ADMINISTERING THE SAME

CROSS REFERENCE OF THE RELATED APPLICATIONS

This application is a Continuation of PCT International Application No. PCT/JP2015/060427 filed on Apr. 2, 2015, which claims priority under 35 U.S.C. 119(a) to Japanese Patent Application No. 2014-077603 filed on Apr. 4, 2014. Each of the above applications is hereby expressly incorporated by reference, in its entirety, into the present application.

BACKGROUND OF THE INVENTION

1. Field of the Invention

The present invention relates to an inactivated whole virion influenza vaccine-containing microneedle array.

2. Description of the Related Art

Influenza is an influenza virus-induced acute infectious respiratory disease that spreads through respiratory droplet transmission. The inoculation of an influenza vaccine is considered to be an effective method for preventive influenza, and in recent years, particularly, prepandemic vaccines against novel influenza have been developed.

Influenza vaccines are classified into three types consisting of a live attenuated vaccine, an inactivated whole virion vaccine, and an inactivated split vaccine. Currently, in Japan, the inactivated split vaccine is widely used.

As an efficient vaccine administration method, a method of administering an influenza vaccine by using a microneedle array has been suggested. JP2007-530680A discloses a transdermal delivery device and an administration method of an influenza vaccine.

WO2010/001671A discloses a microneedle device including microneedles made of polylactic acid coated with an influenza vaccine consisting of antigens composed of type A strains (H1N1 and H3N2) and a type B strain as active components.

In The Academy of Pharmaceutical Science and Technology, Japan, Proceedings of the $28^{TH}$ Annual Conference, verbal announcement No. 23-3-14 "Analysis of immunity-inducing characteristics of transdermal influenza vaccine preparation in clinical research", an intradermal dissolution-type microneedle loaded with a trivalent seasonal influenza HA antigen is prepared, and the immunity-inducing characteristics thereof in a human being are evaluated.

SUMMARY OF THE INVENTION

Although the inactivated split vaccine is widely used in Japan, the efficacy thereof is low. Furthermore, in a case where a pandemic of influenza is taken into consideration, it is important to induce immunity in many people with a small amount of vaccine, and an efficient and simple administration method of the vaccine is required.

in JP2007-530680A, a correlation between a dose of the influenza vaccine administered by the transdermal delivery device and an amount of antibodies produced was not confirmed. In WO2010/001671A and The Academy of Pharmaceutical Science and Technology, Japan, Proceedings of the $28^{TH}$ Annual Conference, verbal announcement No. 23-3-14 "Analysis of immunity-inducing characteristics of transdermal influenza vaccine preparation in clinical research", a method of administering an influenza vaccine by using a microneedle array as described above is examined. However, in these documents, a split vaccine is used, and an amount of antibodies produced is insufficient relative to a dose of the vaccine. Accordingly, there is a strong demand for developing a better microneedle array which makes it possible to efficiently and simply administer an influenza vaccine.

An object of the present invention is to provide a microneedle array which can improve an antibody production ability and makes it possible to administer an influenza vaccine simply.

Under the circumstances described above, the inventors of the present invention repeated intensive examination. As a result, they obtained the knowledge that by administering a microneedle array prepared by combining a needle portion, which contains an inactivated whole virion influenza vaccine, with a sheet portion, an excellent antibody production ability is obtained. Based on this knowledge, the inventors accomplished the present invention.

The present invention provides the following.

[1] A microneedle array including a needle portion containing an inactivated whole virion influenza vaccine and a sheet portion.

[2] The microneedle array described in [1], in which the needle portion contains a water-soluble polymer and dissolves after being inserted into a body.

[3] The microneedle array described in [2], in which the water-soluble polymer is at least one kind of polymer selected from the group consisting of hydroxyethyl starch, dextran, sodium chondroitin sulfate, sodium hyaluronate, carboxymethyl cellulose, polyvinyl pyrrolidone, polyoxyethylene polyoxypropylene glycol, and polyethylene glycol.

[4] The microneedle array described in any one of [1] to [3], in which the influenza vaccine is at least one kind of vaccine selected from the group consisting of an A/H1N1 type, an A/H3N2 type, an A/H5N1 type, and a B type.

[5] The microneedle array described in any one of [1] to [4], in which 90% by mass or more of the inactivated whole virion influenza vaccine with respect to a total mass of the vaccine is contained in a region that accounts for not more than 80% of a height of the needle portion from a tip of the needle portion.

[6] The microneedle array described in any one of [1] to [4], in which 90% by mass or more of the inactivated whole virion influenza vaccine with respect to a total mass of the vaccine is contained in a region that extends not longer than 500 μm from a tip of the needle portion.

[7] An administration method in which the microneedle array described in any one of [1] to [6] is administered and then administered secondly after an interval of equal to or greater than 24 hours and less than 2 months.

In a case where the microneedle array of the present invention is used, an inactivated whole virion influenza vaccine can be administered by a simpler operation, and an antibody production ability can be further improved with a small amount of vaccine, as compared with in a case where the vaccine is administered by injection.

BRIEF DESCRIPTION OF THE DRAWINGS

FIG. 8 is a view in which a group administered with a microneedle array of an H1N1-type inactivated whole virion influenza vaccine, a group administered with a microneedle array of a split influenza vaccine, and groups administered with each of the above vaccines by injection are compared with each other regarding an IgG antibody titer.

FIG. 9 is a view in which a group administered with a microneedle array of an H1N1-type inactivated whole virion influenza vaccine, a group administered with a microneedle array of a split influenza vaccine, and groups administered with each of the above vaccines by injection are compared with each other regarding a virus titer.

DESCRIPTION OF THE PREFERRED EMBODIMENTS

Hereinafter, specific embodiments of the present invention will be described in detail, but the present invention is not limited to the following embodiments. Furthermore, within a range of the object of the present invention, the present invention can be embodied by being appropriately modified.

FIG. 1 is a sectional view showing an example of a microneedle array of the present invention. As shown in FIG. 1, the microneedle array of the present invention is formed of a needle portion 11, which contains an inactivated whole virion influenza vaccine, and a sheet portion 12.

The microneedle array of the present invention contains an inactivated whole virion influenza vaccine.

The inactivated whole virion influenza vaccine means virions that are inactivated in a state of maintaining the form of virus from a virus suspension obtained by culturing influenza viruses, and does not include a split vaccine.

The type of the influenza vaccine is not particularly limited, and includes types A and B, a seasonal vaccine, and a pandemic vaccine. The type A influenza virus includes subtypes which are combinations of a type selected from H1 to H16 and a type selected from N1 to N9. In the present invention, at least one kind of virus selected from the group consisting of an A/H1N1 type, an A/H3N2 type, an A/H5N1 type, and a B type is preferable.

The microneedle array of the present invention includes a needle portion. The needle portion contains an inactivated whole virion influenza vaccine. By puncturing the skin or the mucous membrane by using the needle portion, the influenza vaccine can be transdermally or transmucousally administered.

The shape of the needle portion is not particularly limited as long as the needle portion has a convex structure having a tip. The shape of the needle portion includes a needle shape having a sharp tip and a shape having a tip that is not sharp, and between these, a shape having a sharp tip is preferable. Specifically, examples of the structure of the needle portion include a polygonal pyramidal structure such as a conical structure, a triangular pyramidal structure, or a square pyramidal structure, a polygonal prismoidal structure such as a conical prismoidal structure, a triangular prismoidal structure, or a square prismoidal structure, and the like. Among these, a conical structure, a triangular pyramidal structure, and a square pyramidal structure are preferable, and a conical structure is more preferable.

As shown in needle portions 21 and 22 in FIG. 2 and needle portions 31 to 34 in FIG. 3, the needle portion of the microneedle array of the present invention can have a multilayer structure consisting of two or more layers in which a slope of a lateral surface of the needle portion discontinuously changes. In a case where the needle portion has a multilayer structure, the layers are called a first needle portion layer and a second needle portion layer in this order from a layer including the needle tip. As shown in a first needle portion layer 21 and a second needle portion layer 22 in FIG. 2 or a first needle portion layer 31 and a third needle portion layer 33 in FIG. 3, it is preferable that an angle θ2 formed between lateral surfaces in at least one layer, which is closer to the sheet portion than the first needle portion layer is, (in a case of the second needle portion layer 22 in FIG. 2 and the third needle portion layer 33 in FIG. 3, an angle formed at an intersection point formed when the lateral surfaces are extended in the needle tip direction) is greater than an angle θ1 formed between lateral surfaces in the first needle portion layer. If the above structure is adopted, a total volume of the needle portion is increased, and accordingly, it is possible to make more drug concentrated in an upper end portion of the needle portion at the time of preparing the microneedle array.

The needle portion of the microneedle array of the present invention may have a structure in which the angle formed between the lateral surfaces continuously changes as shown in a needle portion 41 in FIG. 4.

In the needle portion of the microneedle array of the present invention, it is preferable that the inactivated whole virion influenza vaccine is efficiently concentrated in the upper end portion of the needle portion as shown in an upper end portion 51 of the needle portion in FIG. 5. If the above structure is adopted, administration efficiency can be further improved. Furthermore, it is preferable to adopt the above structure because then the same material can be selected for a lower end portion of the needle portion and the sheet portion and hence manufacturing efficiency is improved.

A height of the needle portion is represented by a length of a perpendicular drawn down to the sheet portion from the needle tip, as represented by H in FIG. 1. The height of the needle portion is preferably equal to or greater than 50 μm and equal to or less than 2,000 μm, more preferably equal to or greater than 100 μm and equal to or less than 1,500 μm, and even more preferably equal to or greater than 200 μm and equal to or less than 1,000 μm. If the height of the needle portion is equal to or greater than 50 μm, the inactivated whole virion influenza vaccine can be transdermally administered. If the height of the needle portion is equal to or less than 2,000 μm, it is possible to efficiently cause Langerhans cells, which are effective for inducing immunity, to recognize the vaccine that becomes an antigen.

As shown in a plane 13 of FIGS. 1 to 7, an interface between the needle portion and the sheet portion is called a base portion of the needle portion. A width of the needle portion in the base portion is represented by a distance between points farthest away from each other in the base portion of a single needle, as represented by W in FIGS. 6 and 7. The width of the needle portion in the base portion is preferably equal to or greater than 50 μm and equal to or less than 2,000 μm, more preferably equal to or greater than 100 μm and equal to or less than 1,500 μm, and even more preferably equal to or greater than 200 μm and equal to or less than 1,000 μm.

Then number of needle portions disposed in a single microneedle array is preferably 1 to 2,000, more preferably 3 to 1,000, and even more preferably 5 to 500. In a case where a single microneedle array includes two needle portions, an interval between the needle portions is represented by a distance between foots of perpendiculars drawn down to the sheet portion from the tip of the needle portion, as represented by D in FIG. 1. In a case where a single microneedle array includes three or more needle portions, distances between foots of perpendiculars, which are drawn down to the sheet portion from the tip, of needle portions closest to each other are determined for all of the needle portions, and an average thereof represents the interval between the arrayed needle portions. For example, in a case where the needle portions are arrayed at an equal interval, an aspect in which the interval is represented by D as in FIGS. 6 and 7 is exemplified. The interval between the needle portions is preferably equal to or greater than 0.1 mm and equal to or less than 10 mm, more preferably equal to or greater than 0.2 mm and equal to or less than 5 mm, and even more preferably equal to or greater than 0.3 mm and equal to or less than 3 mm.

Figure 6:
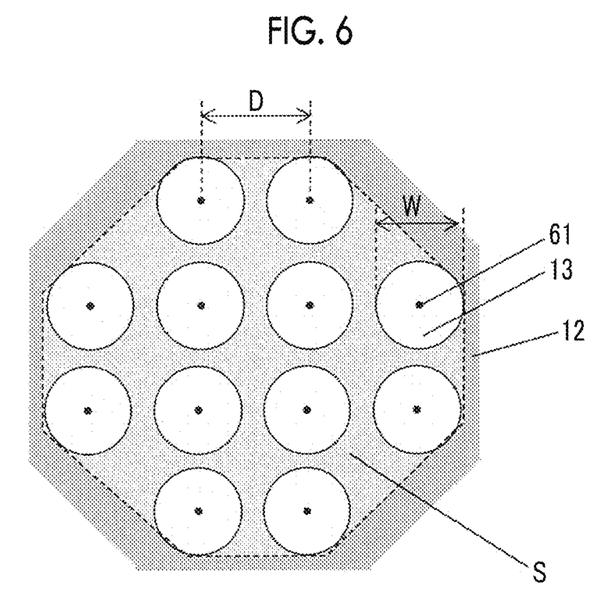
FIG. 6 is a top view of an example of a microneedle array of the present invention.
Figure 7:
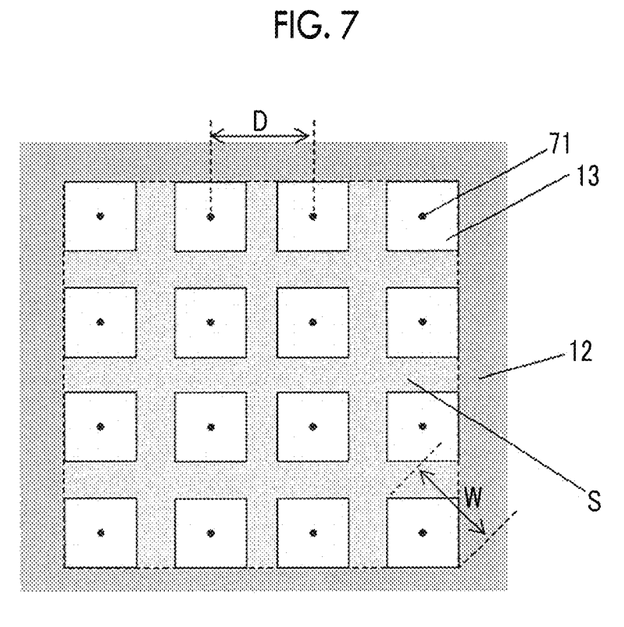
FIG. 7 is a top view of an example of a microneedle array of the present invention.

An area of occupancy of the needle portions in a single microneedle array is indicated by an area of a figure that is constituted to include base portions of all of the needles and to have a minimum area on a tangent of the base portion of a needle in the outermost periphery, as represented by S in FIGS. 6 and 7. The area of occupancy of the needle portion is preferably 0.005 to 1,000 mm$^2$, more preferably 0.05 to 500 mm$^2$, and even more preferably 0.1 to 300 mm$^2$.

In a case where a single microneedle array includes two or more needle portions, a density of the needle portions is represented by a value obtained by dividing the number of needle portions in a single microneedle array by the area of occupancy of the needle portions. The density of needle portions is preferably 0.01 to 10 needles/1 mm$^2$, more preferably 0.05 to 5 needles/1 mm$^2$, and even more preferably 0.1 to 5 needles/1 mm$^2$.

It is preferable that the needle portion dissolves after being inserted into a body after the skin or the mucous membrane is punctured by the needle portion. Therefore, a material constituting the needle portion is preferably a water-soluble polymer, more preferably polysaccharides, and even more preferably at least one kind of polymer selected from the group consisting of hydroxyethyl starch, dextran, sodium chondroitin sulfate, sodium hyaluronate, carboxymethyl cellulose, polyvinyl pyrrolidone, polyoxyethylene polyoxypropylene glycol, and polyethylene glycol.

The microneedle array of the present invention has a sheet portion supporting the needle portion.

When the skin or the mucous membrane is punctured by the needle portion, a user applies force to the sheet portion, and in this way, the inactivated whole virion influenza vaccine contained in the needle portion can be transdermally administered.

A method for applying force to the needle portion is not particularly limited.

A thickness of the sheet portion is represented by a distance between a surface of the sheet portion that contacts the needle and the other surface thereof on the opposite side, as represented by T in FIGS. 1 to 5. The thickness of the sheet portion is preferably equal to or greater than 1 μm and equal to or less than 1,200 μm, more preferably equal to or greater than 3 μm and equal to or less than 600 μm, and even more preferably equal to or greater than 5 μm and equal to or less than 400 μm.

A material constituting the sheet portion is preferably a water-soluble polymer, more preferably polysaccharides, and even more preferably at least one kind of polymer selected from the group consisting of hydroxyethyl starch, dextran, sodium chondroitin sulfate, sodium hyaluronate, carboxymethyl cellulose, polyvinyl pyrrolidone, polyoxyethylene polyoxypropylene glycol, and polyethylene glycol.

The material constituting the sheet portion and the material constituting the needle portion may be the same as or different from each other.

Figure 1:
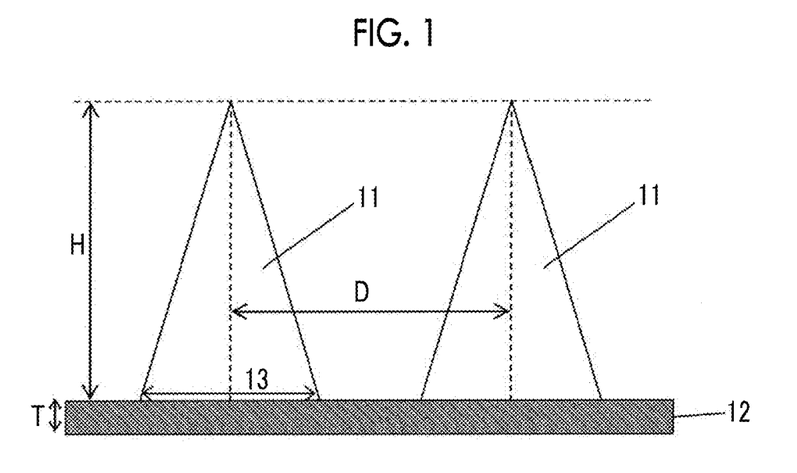
FIG. 1 is sectional view showing an example of a microneedle array of the present invention.
Figure 2:
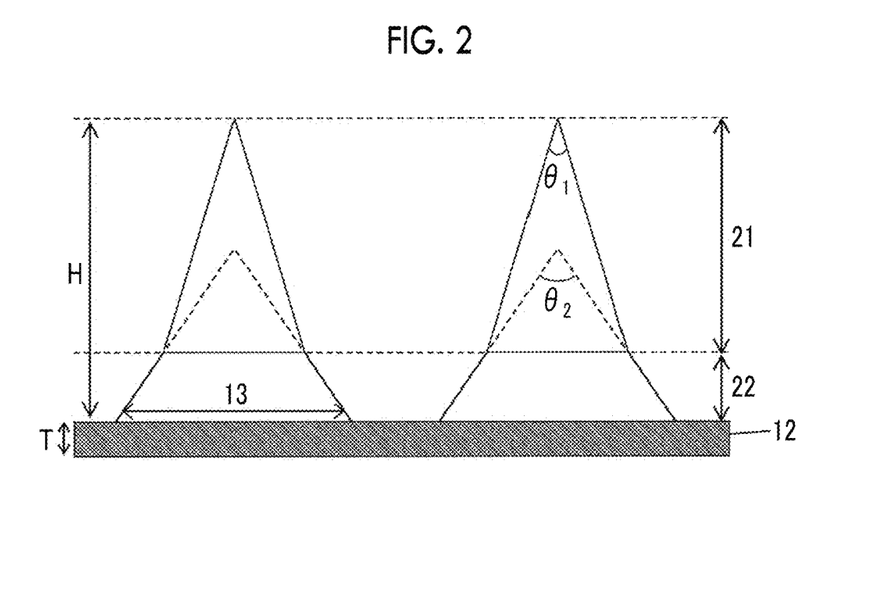
FIG. 2 is a sectional view showing an example of a microneedle array of the present invention.
Figure 3:
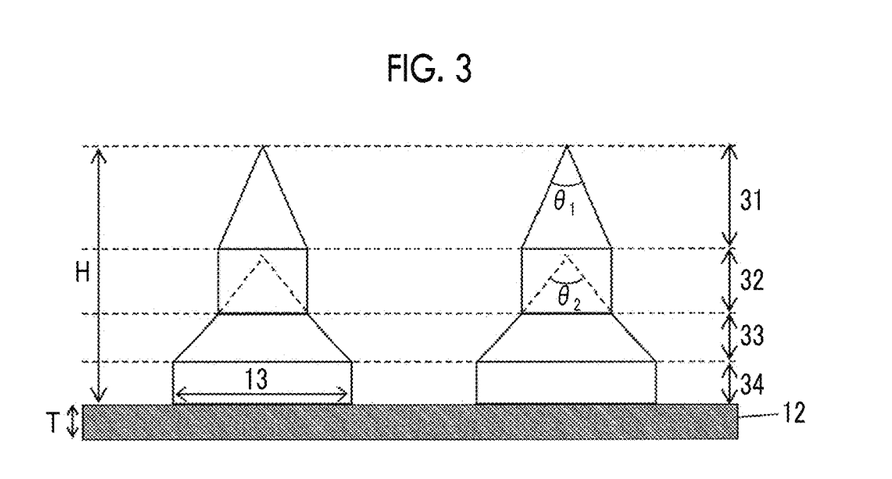
FIG. 3 is a sectional view showing an example of a microneedle array of the present invention.
Figure 4:
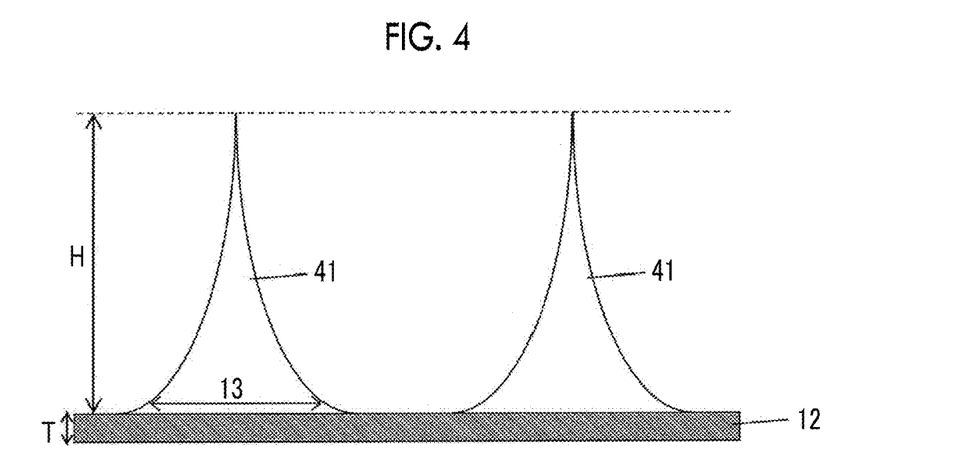
FIG. 4 is a sectional view showing an example of a microneedle array of the present invention.
Figure 5:
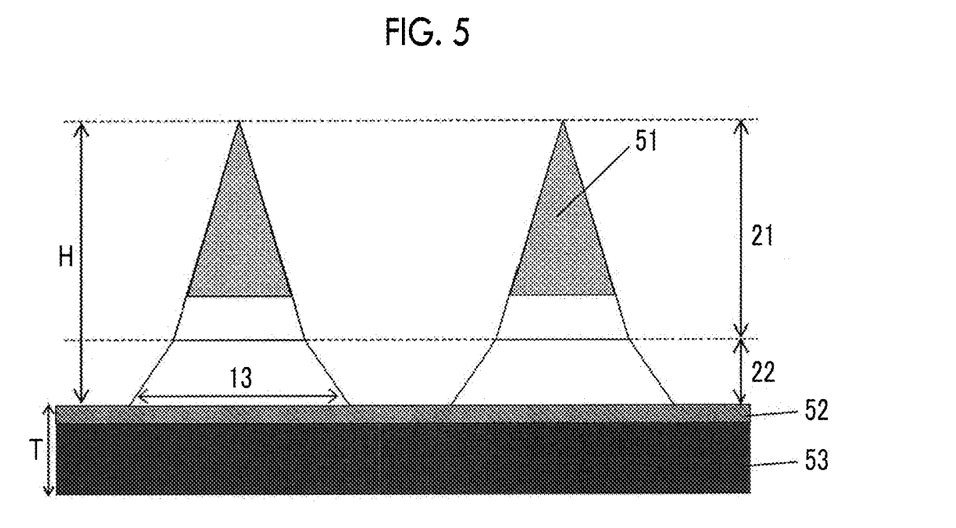
FIG. 5 is a sectional view showing an example of a microneedle array of the present invention.

As shown in a sheet portion 52 of FIG. 5, the microneedle array of the present invention can include a support in a portion of the sheet portion. If the microneedle array includes the support, the strength of the sheet portion is enhanced, and hence the skin or the mucous membrane can be more simply punctured by the microneedle array.

A material of the support is not particularly limited. In view of convenience of puncturing, examples of the material include polyethylene terephthalate, polyethylene naphthalate, and the like.

A thickness of the support is preferably equal to or greater than 10 μm and to or less than 1,000 μm, more preferably equal to or greater than 30 μm and equal to or less than 500 μm, and even more preferably equal to or greater than 50 μm and equal to or less than 300 μm.

90% by mass or more of the inactivated whole virion influenza vaccine contained in the microneedle array of the present invention with respect to a total mass of the vaccine is preferably contained in a region that accounts for not more than 80% of a height of the needle portion from the tip of the needle portion, more preferably contained in a region that accounts for not more than 60% of the height of the needle portion from the tip of the needle portion, and even more preferably contained in a region that accounts for not more than. 40% of the height of the needle portion from the tip of the needle portion.

Furthermore, 90% by mass or more of the inactivated whole virion influenza vaccine contained in the microneedle array of the present invention with respect to a total mass of the vaccine is preferably contained in a region that extends not longer than 500 μm from the tip of the needle portion, more preferably contained in a region that extends not longer than 350 μm from the tip of the needle portion, and even more preferably contained in a region that extends not longer than 200 μm from the tip of the needle portion.

A manufacturing method of the microneedle array of the present invention is not particularly limited. It is preferable that the microneedle array is obtained by a manufacturing method including (1) a step of manufacturing a mold, (2) a step of preparing an inactivated whole virion influenza vaccine and a water-soluble polymer, (3) a step of forming an upper end portion of a needle portion by filing the mold with a liquid obtained in the step (2), (4) a step of forming a lower end portion of the needle portion and a sheet portion by filling the mold with the water-soluble polymer, and (5) a step of peeling the microneedle array from the mold.

From the viewpoint of improving compliance, an administration time of the microneedle array of the present invention is preferably within 1 hour, and more preferably within 30 minutes.

From the viewpoint of improving an antibody production ability; the microneedle array of the present invention is preferably administered twice. An administration interval is preferably about 24 hours to 2 months, more preferably about 3 days to 1.5 months, and even more preferably about 1 week to 4 weeks.

The microneedle array of the present invention can improve an antibody production ability by stimulating immune response in the skin. Specifically, the microneedle array can increase a serum IgG antibody titer.

Furthermore, it was found that by administering twice the microneedle array of the present invention, titers of antibodies against other types of influenza viruses increased.

EXAMPLES

Hereinafter, the microneedle array of the present invention will be more specifically described based on examples, but the present invention is not limited to the following examples.

Example 1

Preparation of Whole Virion Influenza Vaccine-Containing Microneedle Array

An influenza virus of an A/PR/8/1934(H1N1) strain was treated with formalin, thereby obtaining an inactivated whole virion vaccine. A mold having a conical depression was filled with a 14.4% by mass hydroxyethyl starch solution, to which the inactivated whole virion vaccine was added, followed by drying.

Then, the mold was filed with 40% by mass sodium chondroitin sulfate, followed by drying, thereby forming the rest of needle portions and a sheet portion (containing polyethylene terephthalate as a support). The resultant was released from the mold, thereby preparing an inactivated whole virion vaccine-containing microneedle array of Example 1 having a double layer structure in which the needle portions had a height of about 580 μm (first needle portion layer: conical structure having a height of about 460 μm and a bottom surface diameter of about 270 μm; second needle portion layer: conical prismoidal structure having a height of about 120 μm, an upper bottom surface diameter of about 270 μm, and a lower bottom surface diameter of about 460 μm; width of base portion of needle portion: about 460 μm; thickness of sheet portion: about 205 μm (about 175 μm of the sheet portion was composed of polyethylene terephthalate); number of needles: 9; interval between needles: about 1 mm; area of occupancy of needle portions: 6 $mm^2$; density of needles: about 1.5 needles/$mm^2$). According to the amount of the hydroxyethyl starch solution tilling the mold, the amount of the inactivated whole virion vaccine added to the hydroxyethyl starch solution was varied, in this way, microneedle arrays with a vaccine content of 0.67 ng, 1.3 ng, 2.7 ng, 5.4 ng, 11 ng, 21 ng, 0.11 μg, and 0.54 μg in terms of a hemagglutinin content equivalent were prepared.

A distribution of the inactivated whole virion vaccine in the needle portions of the prepared microneedle array was estimated by the following method.

A microneedle array was prepared by the same method as described above, except that, instead of the inactivated whole virion vaccine, a 14.4% by mass hydroxyethyl starch solution containing a 0.1% by mass Evans blue dye was used. The microneedle array was cut in a direction horizontal to the sheet portion at a side 140 μm distant from the tip of the needle portion, a portion including the cut needle tip and a portion including both of the rest of the needle portion and the sheet portion were separately dissolved in water, and an absorbance thereof was measured. In this way, a proportion of the dye distributed to the portion including the needle tip was measured. The proportion was 45%. The microneedle array was cut at sides 200 μm, 260 μm, and 330 μm distant from the tip of the needle portion, and at this time, a proportion of the dye distributed to the portion including the needle tip was measured in the same manner as described above. The proportion was 90%, 100%, and 100% respectively.

Comparative Example 1

Preparation of Split Influenza Vaccine-Containing Microneedle Array

An influenza virus of an A/PR/8/1934(H1N1) strain was treated with ether, thereby obtaining a split vaccine. Then, by using the split vaccine instead of the inactivated whole virion vaccine, a microneedle array of Comparative Example 1 was prepared and obtained by the same operation as in Example 1. According to the amount of the hydroxyethyl starch solution filling the mold, the amount of the split vaccine added to the hydroxyethyl starch solution was varied. In this way, microneedle arrays with a vaccine content of 21 ng, 0.11 μg, and 0.54 μg in terms of a hemagglutinin content equivalent were prepared.

Vaccine Administration Test Performed on Mouse by Using Microneedle Array (Example 1 and Comparative Example 1)

Mice (Balb/c (CLEA Japan, Inc.), female, 7-week old) were purchased, tamed for 1 week, and then subjected to an influenza vaccine administration test. In Example 1 and Comparative Example 1, the hair of the back of the mice was removed under anesthesia, and then the back of the mice was punctured for 4 minutes with the microneedle array in a state where their skin was stretched. In both of Example 1 and Comparative Example 1, the test was performed on 4 mice.

Vaccine Administration Test Performed on Mouse by Subcutaneous Injection Test (Comparative Examples 2 and 3)

As Comparative Examples 2 and 3, under the same conditions as in Example 1 and Comparative Example 1, a vaccine was administered to mice by subcutaneous injection. In Comparative Example 2, 100 μL of a vaccine, which was obtained by diluting the inactivated whole virion vaccine prepared in Example 1 with water for injection, was administered in an amount of 2.7 ng, 5.4 ng, 11 ng, 21 ng, 43 ng, 0.21 μg, and 1.1 μg respectively in terms of a hemagglutinin content equivalent. In Comparative Example 3, 100 μL of a vaccine, which was obtained by diluting the split vaccine prepared in Comparative Example 1 with water for injection in respective doses, was administered in an amount of 43 ng, 0.21 μg, and 1.1 μg respectively in terms of a hemagglutinin content equivalent. In both of Comparative Examples 2 and 3, the test was performed on 4 mice.

Evaluation of Amount of Antibody Produced in Mouse Serum by the Administration of Example 1 and Comparative Examples 1 to 3

After the administration, the mice raised for 4 weeks were subjected to laparotomy under anesthesia, and blood was collected from their caudal vena cava. The blood allowed to stand at room temperature was subjected to centrifugation, and the supernatant was collected, thereby obtaining serum. The amount of an influenza-specific antibody (IgG) contained in the obtained serum was measured by the following method.

(Measurement of Amount of IgG Antibody Produced)

A virus antigen inactivated for ELISA was dispensed at 50 μL/well into NUNC immunoplate maxisorp (C bottom, 96 well), and the plate was sealed and allowed to stand overnight at 4° C. After standing, the plate was washed 4 times with PBST (Gibco PBS+0.1% Tween). Then, a blocking buffer (50 mM Tris (pH 8.0), 1% BSA) was added dropwise thereto at 200 μL/well and the plate was allowed to stand for 30 minutes at room temperature. After standing, the plate was washed 4 times with PBST (Gibco PBS +0.1% Tween). After washing, a sample diluted about 10,000× with a diluent (50 mM Tris (pH 8.0), 1% BSA, 0.1% Tween) was added dropwise to the plate at 100 μL/well, and the plate was allowed to stand for 1 hour at room temperature. After standing, the plate was washed again 4 times with PBST (Gibco PBS+0.1% Tween).

Thereafter, an HRP-labeled anti-mouse IgG antibody diluted (500×) with a diluent (50 mM Tris (pH 8.0), 1% BSA, 0.1% Tween) was added dropwise to the plate at 100 μL/well, and the plate was allowed to stand for 1 hour at room temperature. After standing, the plate was washed again 4 times with PBST (Gibco PBS+0.1% Tween).

Furthermore, to cause a substrate reaction, TMB was added dropwise to the plate at 100 μL/well, and the plate was allowed to stand for 15 minutes at room temperature in a state of being shielded from light. Then, a stop buffer (1 mol/L HCl) was added dropwise thereto at 100 μL/well.

After the dropwise addition, an absorbance (reference: 620 nm) at λ=450 nm was measured, and an amount of IgG antibody produced was relatively evaluated based on the magnitude of absorbance.

Figure 8:
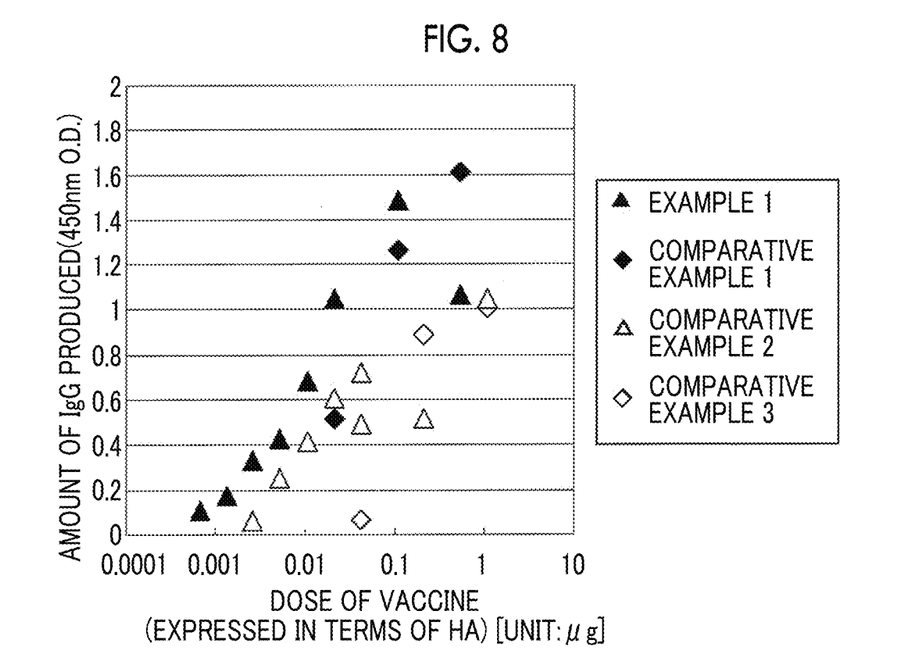

FIG. 8 shows the evaluation of the amount of IgG antibodies produced in the mouse serum by the administration of Example 1 and Comparative Examples 1 to 3.

It was confirmed that, unexpectedly; even at a low dose, the IgG- antibody was prouced more in a group administered with a vaccine by Example 1. than in a group administered with a vaccine by Comparative Examples 1 to 3.

Example 2

Preparation of Whole Virion Influenza Vaccine-Containing Microneedle Array

By the same method as in Example 1, a microneedle array was prepared which contained an inactivated whole virion vaccine of an influenza virus of an A/PR/8/1934 (H1N1) strain in an amount of 0.01 μg in terms of a hemagglutinin content equivalent.

Comparative Example 4

Preparation of Split Influenza Vaccine-Containing Microneedle Array

By the same method as in Comparative Example 1, a microneedle array was prepared which contained a split vaccine of an influenza virus of an A/PR/8/1934 (H1N1) strain in an amount of 0.01 μg in terms of a hemagglutinin content equivalent.

Vaccine Administration Test Performed on Mouse by Using Microneedle Array (Example 2 and Comparative Example 4)

Mice (Balb/c (CLEA Japan, Inc.), female, 7-week old) were purchased, tamed for 1 week, and then subjected to an influenza vaccine administration test. In Example 2 and Comparative Example 4, the hair of the back of the mice was removed under anesthesia, and then the back of the mice was punctured for 4 minutes with the microneedle array in a state where their skin was stretched. In both of Example 2 and Comparative Example 4, the test was performed on 6 mice.

Vaccine Administration Test Performed on Mouse by Subcutaneous Injection Test (Comparative Examples 5 and 6)

As Comparative Examples 5 and 6, under the same conditions as in Example 2 and Comparative Example 4, a vaccine was administered to mice by subcutaneous injection. In Comparative Example 5, 100 μL of a vaccine, which was obtained by diluting the inactivated whole virion vaccine prepared in Example 2 with physiological saline, was administered in an amount of 0.01 μg in terms of a hemagglutinin content equivalent. In Comparative Example 6, 100 μL of a vaccine, which was obtained by diluting the split vaccine prepared in. Comparative Example 4 with water for injection in respective doses, was administered in an amount of 0.01 μg in terms of a hemagglutinin content equivalent. In both of Comparative Examples 5 and 6, the test was performed on 6 mice.

Evaluation of Viral Multiplication Inhibitory Effect on Mouse Administered with Vaccine of Example 2 and Comparative Examples 4 to 6

Under anesthesia, 300 μL of an influenza virus (virus titer: $10^4$ pfu) of an A/PR/8/1934 (H1N1) strain diluted with PBS was transnasally administered to the mice rasied for 4 weeks after the administration described above. 3 days after the administration, the mice's lungs were extracted under anesthesia, and a culture medium containing 1× MEM/BSA/antibiotics was added to the pulmonary emulsion at a ratio of 1:9. The resulting mixture was subjected to a pulverization treatment using a multibead shocker, thereby obtaining a 10% pulmonary emulsion.

(Measurement of Virus Titer in Lung)

MDCK cells were seeded onto 12-well plate and incubated for 2 days at 37° C. such that the cells were cultured and covered the entire bottom surface of the plate. 100 μL of pulmonary emulsions that were obtained by diluting the aforementioned pulmonary emulsion with 1× MEM buffer to 10× to 1,000,000× by a factor of 10 were added respectively in an amount of 1 mL to the 12-well plate in which the MDCK cells were cultured, followed by incubation for 1 day at 35° C. The pulmonary emulsions were washed off, 1 mL of a mixture (42° C.) of a 1× MEM buffer and 1% agarose was then added to each well, and the plate was cooled to room temperature so as to cause gelation. The 12-well plate was incubated for 2 days at 35° C. Thereafter, 1 mL of a mixture (42° C.) of a 1× MEM buffer and 1 % agarose that contained 0.005% neutral red was added to each well, and the plate was further incubated for 1 day at 35° C. Then, the 12-well plate was put upside down on a light table, and the number of viral plaques (debris of cells that died of infection) were counted. By using a dilution factor at which the number of plaques per well became equal to or greater than 10 and less than 100, a virus titer was determine. In a case where k plaques were formed in a well to which the pulmonary emulsion was added at a dilution factor of 10 to the power of n, a virus titer was calcuated by the following equaiton as a plaque formation unit (log(pfu/g)) per 1 g of the pulmonary emulsion.

$$T=\log(k\times 10^{(n+2)})$$

Figure 9:
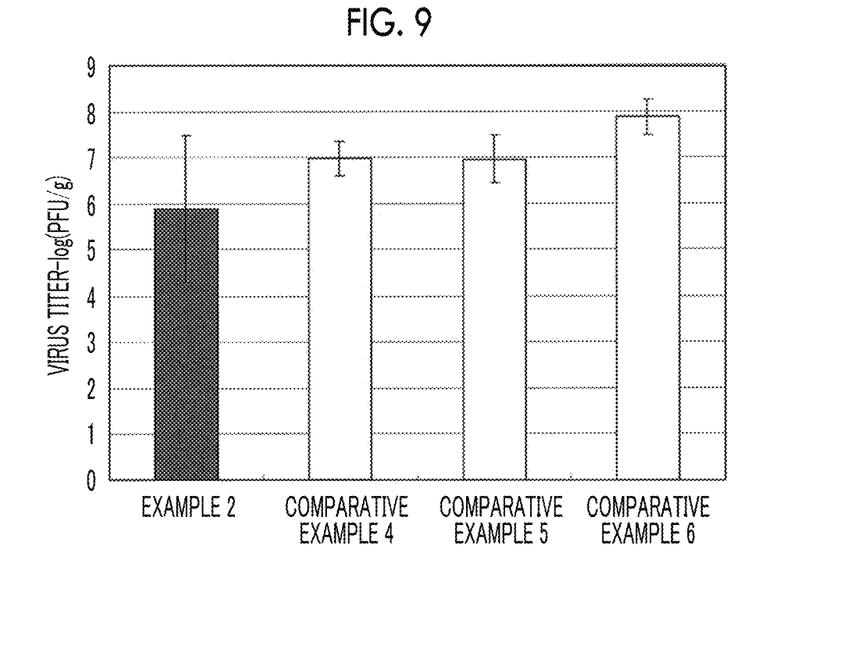

FIG. 9 shows the results of measurement of the amount of virus in the lung resulting from the administration of Example 2 and Comparative Examples 4 to 6.

The amount of virus was smaller in a group administered with a vaccine by Example 2 than in a group administered with a vaccine by Comparative Examples 4 to 6, and accordingly, it was confiremd that Example 2 exerted a strong viral multiplication inhibitory effect in the lung.

EXPLANATION OF REFERENCES

11: needle portion
12: sheet portion

13: base portion
21: first needle portion layer
22: second needle portion layer
31: first needle portion layer
32: second needle portion layer
33: third needle portion layer
34: fourth needle portion layer
41: needle portion
51: upper end portion needle portion
52: sheet portion
53: support
61: tip of conical needle portion
71: tip of square pyramidal needle portion
D: interval between needle portions
H: height of needle portion
S: area of occupancy of needle portion
T: thickness of sheet portion
W: width of base portion of needle portion
θ1: angle formed between lateral surfaces of first needle portion layer
θ2: angle formed between lateral surfaces of second or third needle portion layer

What is claimed is:

1. A microneedle array comprising:
a needle portion containing an inactivated whole virion influenza vaccine; and
a sheet portion,
wherein 90% by mass or more of the inactivated whole virion influenza vaccine with respect to the total mass of the vaccine is contained in a region that accounts for not more than 60% of the height of the needle portion from a tip of the needle portion; and
the height of the needle portion is equal to or greater than 50 μm and equal to or less than 2,000 μm, and
wherein the needle portion contains a water-soluble polymer, and the water-soluble polymer contains at least hydroxyethyl starch.

2. The microneedle array according to claim 1, wherein the needle portion dissolves after being inserted into a body.

3. The microneedle array according to claim 1, wherein the influenza vaccine is at least one kind of virus selected from the group consisting of an A/H1N1 type, an A/H3N2 type, an A/H5N1 type, and a B type.

4. The microneedle array according to claim 2, wherein the influenza vaccine is at least one kind of virus selected from the group consisting of an A/H1N1 type, an A/H3N2 type, an A/H5N1 type, and a B type.

5. An administration method, wherein the microneedle array according to claim 1 is administered to skin or mucous membrane and then administered secondly to the skin or mucous membrane after an interval of equal to or greater than 24 hours and less than 2 months.

6. An administration method, wherein the microneedle array according to claim 2 is administered to skin or mucous membrane and then administered secondly to the skin or mucous membrane after an interval of equal to or greater than 24 hours and less than 2 months.

7. An administration method, wherein the microneedle array according to claim 3 is administered to skin or mucous membrane and then administered secondly to the skin or mucous membrane after an interval of equal to or greater than 24 hours and less than 2 months.

* * * * *